(12) United States Patent
Amir et al.

(10) Patent No.: US 9,958,417 B2
(45) Date of Patent: May 1, 2018

(54) NON-TRAVERSING TUBE INSPECTION SYSTEM

(71) Applicant: Arise Global Pte. Ltd., Singapore (SG)

(72) Inventors: Noam Amir, Ness-Ziona (IL); Dov Furman, Rehovot (IL); Harel Primack, Rishon LeZion (IL); Silviu Zilberman, Rishon Le-Zion (IL)

(73) Assignee: ARISE GLOBAL PTE. LTD, Singapore (SG)

( * ) Notice: Subject to any disclaimer, the term of this patent is extended or adjusted under 35 U.S.C. 154(b) by 368 days.

(21) Appl. No.: 14/407,331

(22) PCT Filed: Jun. 10, 2013

(86) PCT No.: PCT/IL2013/000054
§ 371 (c)(1),
(2) Date: Dec. 11, 2014

(87) PCT Pub. No.: WO2013/186768
PCT Pub. Date: Dec. 19, 2013

(65) Prior Publication Data
US 2015/0122030 A1    May 7, 2015

Related U.S. Application Data

(60) Provisional application No. 61/658,038, filed on Jun. 11, 2012, provisional application No. 61/763,456, filed on Feb. 11, 2013.

(51) Int. Cl.
*G01N 29/24* (2006.01)
*G01M 5/00* (2006.01)
*G01N 29/04* (2006.01)

(52) U.S. Cl.
CPC ........ *G01N 29/043* (2013.01); *G01M 5/0033* (2013.01); *G01M 5/0066* (2013.01);
(Continued)

(58) Field of Classification Search
CPC .... G01N 29/043; G01N 29/24; G01N 5/0033; G01N 5/0066; G01N 2291/0425; G01N 2291/044; G01N 2291/2636
(Continued)

(56) References Cited

U.S. PATENT DOCUMENTS 4,619,143 A   10/1986  Franken
4,621,532 A   11/1986  Takagi et al.
(Continued)

FOREIGN PATENT DOCUMENTS

EP       0261825       3/1988
JP      2000028586     1/2000
(Continued)

OTHER PUBLICATIONS

AMIR. The Evolution of Acoustic Inspection Based on Acoustic Pulse Reflectometry. Quality Magazine. Jun. 13, 2011. [Retrieved on: Dec. 11, 2014]. Retrieved from Internet: <URL: http://www.qualitymag.com/articles/90186-the-evolution-of-acoustic-inspection-based-on-acoustic-pulse-reflectometry> Entire document.
(Continued)

*Primary Examiner* — J M Saint Surin
(74) *Attorney, Agent, or Firm* — Dorsey & Whitney LLP

(57) ABSTRACT

Tube inspections are performed by combining the use of APR technology with GW technology. The reflections measured by both technologies are compared to each other and used to more specifically identify the type and location of a flaw or anomaly that appears in the interior of the tube. Further, embodiments of novel probes to be used in GW technique for inspecting tubes with mechanical waves having bandwidth that is equal to 150 KHz or more are disclosed.

13 Claims, 4 Drawing Sheets

(52) U.S. Cl.
CPC ....... *G01N 29/24* (2013.01); *G01N 2291/044* (2013.01); *G01N 2291/0425* (2013.01); *G01N 2291/2636* (2013.01)

(58) Field of Classification Search
USPC .......................................................... 73/623
See application file for complete search history.

(56) References Cited

U.S. PATENT DOCUMENTS

| | | | |
|---|---|---|---|
| 5,460,046 A | 10/1995 | Maltby et al. | |
| 5,892,162 A * | 4/1999 | Spinks ................... | B06B 1/045 |
| | | | 73/40.5 A |
| 6,568,271 B2 * | 5/2003 | Shah ...................... | G01N 29/11 |
| | | | 73/599 |
| 7,019,520 B2 * | 3/2006 | Kwun .................... | G01N 27/82 |
| | | | 324/238 |
| 7,634,392 B2 | 12/2009 | Kwun et al. | |
| 7,677,103 B2 | 3/2010 | Amir et al. | |
| 8,960,007 B2 | 2/2015 | Furman et al. | |
| 9,261,484 B1 * | 2/2016 | Juan ...................... | G01N 29/028 |
| 9,671,373 B2 * | 6/2017 | Borigo ................. | G01N 29/043 |
| 2002/0011124 A1 | 1/2002 | Phipps | |
| 2005/0104584 A1 * | 5/2005 | Kwun .................... | G01N 27/82 |
| | | | 324/238 |
| 2007/0034012 A1 | 2/2007 | Amir et al. | |
| 2008/0208505 A1 | 8/2008 | Amir et al. | |
| 2009/0158850 A1 * | 6/2009 | Alleyne ............... | G01N 29/221 |
| | | | 73/623 |
| 2011/0112776 A1 | 5/2011 | Amir et al. | |
| 2011/0166808 A1 | 7/2011 | Primack | |
| 2011/0320139 A1 | 12/2011 | Amir et al. | |
| 2012/0053895 A1 | 3/2012 | Amir et al. | |
| 2012/0227499 A1 | 9/2012 | Amir et al. | |
| 2012/0227501 A1 | 9/2012 | Furman et al. | |
| 2014/0202249 A1 * | 7/2014 | Luo ......................... | G01H 5/00 |
| | | | 73/597 |

FOREIGN PATENT DOCUMENTS

| | | |
|---|---|---|
| JP | 2012107959 | 6/2012 |
| WO | WO1996/012951 | 5/1996 |
| WO | WO2013/186768 | 12/2013 |

OTHER PUBLICATIONS

Harrington et al. Non-invasive techniques to assess drains. Transport Research Laboratory Published Project Report PPR447. Aug. 2010. [Retrieved on Dec. 11, 2014]. Retrieved from Internet: <URL:http://www.transportresearchfoundation.co.uk/PDF/PPR447-Non-invasive-techniques-to-assess-drains-31Aug2010-Reviewed-doc-1.pdf>. Entire Reference.

International Search Report for International application No. PCT/IL2013/000054 dated Jan. 13, 2014.

* cited by examiner

NON-TRAVERSING TUBE INSPECTION SYSTEM

CROSS-REFERENCE TO RELATED APPLICATIONS

This application is being filed under the Patent Cooperation Treaty application and is being filed in the Israeli Receiving Office claiming the benefit of the prior filing date of the U.S. provisional application for patent that was filed on Jun. 11, 2012 bearing the tile of "MULTI-MODALITY NON-TRAVERSING TUBE INSPECTION SYSTEM," and assigned Ser. No. 61/658,038. Further, this application claims the benefit of the prior filing date of the U.S. provisional application for patent that was filed on Feb. 11, 2013 bearing the tile of "MULTI-MODALITY NON-TRAVERSING TUBE INSPECTION SYSTEM," and assigned Ser. No. 61/763,456.

FIELD OF INVENTION

The present invention relates to the field of non-destructive testing and more particularly, the present invention is in the technical field of non-traversing techniques for tube inspection.

DESCRIPTION OF BACKGROUND ART

There are several techniques presently in use for conducting tube inspections. These techniques can be divided into two main groups: traversing and non-traversing. The traversing methods employ a probe which can inspect only the portion of the tube in its immediate vicinity. In order to inspect an entire tube, the probe is tethered to a cable by which the probe is pushed all the way down from one end of the tube to the other, and then pulled back. Traversing methods are slow, prone to wear and tear of the probe, and eventual failure. One example of a traversing inspection method is Eddy Current Testing, and related methods such as Remote Field Testing and Magnetic Flux Leakage testing. All these traversing methods are electromagnetic methods, having varying degrees of accuracy. Another example is the widely known IRIS (Internal Rotating Inspection System), which is based on ultrasound. IRIS is based on use of a probe that scans the tube wall in a spiral manner using an ultrasound beam propagating in water. It is much slower than the electromagnetic methods and requires cleaning the tube wall down to the metal, which is an expensive process.

Non-traversing methods are based on inserting a probe a relatively short distance into a tube under test, and then applying a physical method for inspecting the entire tube from this location. One such method is Acoustic Pulse Reflectometry (APR). In the APR method, an acoustic signal (which could be, for example, but not limited to a pulse or a pseudo noise signal, swept sine, etc) is propagated through the air inside the tube. Any changes in the cross section profile of the tube create reflections which propagate back down to the probe where they can be recorded and later analyzed. APR has good results at detecting anomalies in the interior surface or cross-sectional profile of a tube, such as blockages, through holes, and circumferential changes in cross section of a tube as a few non-limiting examples. APR has several advantages: APR is fast, it can accurately assess blockages, and it is very sensitive to through-holes, for example. A reader who wishes to learn more about APR systems is invited to read U.S. Pat. No. 7,677,103, or US pre-granted publication number US2011-0166808, or U.S. patent application Ser. No. 13/403,984.

A second non-traversing method, known widely as the Guided-Wave (GW) method, is based on propagating mechanical waves within the tube wall itself. These waves can be, for example but not limited to, a torsional or longitudinal wave, and the excitation signal can be for example, but not limited to, a pulse or a pseudo noise signal, swept sine, etc. The GW technique is sensitive mainly to the degree of material loss. Any changes in the tube wall properties or dimensions will create a reflection which can be recorded and analyzed. GW is fast and sensitive to flaws on both the outside and inside surfaces of the tube.

Usually GW non-traversing inspection systems are used for inspecting tubes in which resolution is less critical. In order to improve the resolution of the inspection system high frequency and wide bandwidth is needed. Typically GW non-traversing inspection systems have limited bandwidth.

SUMMARY OF THE DISCLOSURE

In some situations and under some circumstances, APR may not discover small pits in the tube wall. Small pits in the tube wall create relatively small changes in the cross section profile of a tube, thus making the reflected signals small and therefore hard to detect. Furthermore, because APR detects overall changes in the cross section of the tube, it is difficult to determine through APR whether an increase in cross section is created by a deep and narrow pit or by a shallow pit spread over a large portion of the circumference of the tube. Finally, APR is insensitive to any flaws found on the outside surface of the tube and to cracks which do not open into the interior surface of the tube. GW methods may have difficulties in distinguishing between pits and through holes, as well as distinguishing these from blockages in the tube. Hence, there is a need for a non-traversing method that can give a complete solution to the challenge of detection, classification and estimation of blockages, Internal Diameter (ID) or Outer Diameter (OD) wall loss, holes and crack defects in tubes.

In order to detect small defects some possible embodiments of GW method, excite high frequencies to obtain short wavelengths. For example, mechanical waves with frequencies above 200 KHz may be needed in order to detect and size defects of length 2-3 millimeters. At such frequencies multiple modes of propagation will be excited. These modes may have different cut-on frequencies, different dispersion curves, and some of them are not axis symmetric. If these modes are not separated, the interpretation of the measured signal is ambiguous. However, in order to separate these modes, multiple sensors are required around the tube circumference. When inspecting narrow gauge tubes such as those typically found in heat exchangers, it is difficult to fit a sufficient number of sensors into the limited space available.

Increasing the frequency of the propagating mechanical waves in the tube wall causes resonances between the mechanical/electrical transducer and the wall of the inspected tube. The above-described deficiencies of non-traversing methods, do not limit the scope of the inventive concepts of the present disclosure in any manner. The deficiencies are presented for illustration only.

Some embodiments of a novel GW non-traversing inspection system overcome the constraints introduced by the available space for mounting a plurality of transducers in tubes by using two or more rings of transducers. Each ring can be placed at a different axial location relative to the other rings. The transducers on one ring can be placed with a circumferential offset ("staggered") relative to the transducers in another ring. Reflected signals that are received by the different rings can be combined to achieve a higher effective circumferential transducer count. In some embodiments the rings can have a similar number of transducers. In other possible embodiments each ring can have a different number of transducers.

Further, in order to overcome the resonance phenomena associated with the interface between the GW transducers and the tube wall, some embodiments of the novel GW non-traversing inspection system may use a partially-isolating isolating-dry coupling element, which is partially isolating, placed between the GW transducer and the tube wall. This isolation can be achieved by using an attenuating dry coupling element between the GW transducer and the tube wall that suppresses the resonance and increases the bandwidth. In order to overcome the effect of the dry coupling element on the required signal to nose ratio, the transmitted energy can be increased.

In addition some of the disclosed embodiments engage the two modalities, the APR and the novel GW into a single non-traversing system. Engaging the two modalities delivers a complete solution for inspecting the internal Diameter (ID) (anomalies such as blockages, holes, as a non-limiting example) as well as the Outer Diameter (OD) anomalies such as wall loss, holes and crack defects of tubes.

In the following description, for purposes of explanation, numerous specific details are set forth in order to assist in the understanding of the invention. It will be apparent, however, to one skilled in the art that the invention may be practiced without these specific details. In other instances, structures and devices are shown in block diagram form in order to avoid obscuring the invention. References to numbers without subscripts or suffixes are understood to reference all instances of subscripts and suffixes corresponding to the referenced number. Moreover, the language used in this disclosure has been principally selected for readability and instructional purposes, and may not have been selected to delineate or circumscribe the inventive subject matter, resort to the claims being necessary to determine such inventive subject matter.

Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Although some of the following description is written in terms that relate to software or firmware, embodiments may implement the features and functionality described herein in software, firmware, or hardware as desired, including any combination of software, firmware, and hardware. In the following description, the words "unit," "element," "module" and "logical module" may be used interchangeably. Anything designated as a unit or module may be a stand-alone unit or a specialized or integrated module. A unit or a module may be modular or have modular aspects allowing it to be easily removed and replaced with another similar unit or module. Each unit or module may be any one of, or any combination of, software, hardware, and/or firmware, ultimately resulting in one or more processors programmed to execute the functionality ascribed to the unit or module. Additionally, multiple modules of the same or different types may be implemented by a single processor. Software of a logical module may be embodied on a computer readable medium such as a read/write hard disc, CDROM, Flash memory, ROM, or other memory or storage, etc. In order to execute a certain task a software program may be loaded to an appropriate processor as needed. In the present disclosure the terms task, method, process can be used interchangeably.

The present disclosure describes several examples of a novel GW probe as well as several examples of a novel multi-modality-Non-Traversing Tube Inspection (MMNTTI) technique. The novel MMNTTI combines APR techniques with the novel GW techniques. An example system of an MMNTTI can comprise a probe creating guided mechanical waves in the tube wall and measuring the reflected waves, while also creating acoustic waves in the air inside the tube and measuring their reflections. An embodiment of an MMNTTI probe can have a plurality of transducers. The plurality of transducers required for APR and GW are fit into a module which may be detachable from the probe. For each tube diameter or range of diameters, a different detachable module can be used. Examples of a novel GW probe can be similar to an MMNTTI probe without the APR transducers, for example.

After inserting the probe into a tube to be inspected, an example embodiment of an MMNTTI system may transmit an acoustic signal (which could be for example, but not limited to, a pulse or a pseudo noise signal, swept sine, etc). The acoustic signal can propagate in the air inside the tube and create reflections received from changes in the tube cross section. The reflections can be recorded and later analyzed. Then the probe may transmit mechanical waves in the tube wall. The mechanical waves can be but not limited to torsional or longitudinal waves, and the excitation signal can be, for example but not limited to, a pulse or a pseudo-noise signal, swept sine. Any changes in the tube wall properties or dimensions will create a reflection which can be recorded and analyzed. In some embodiments, the GW and APR measurements can be performed simultaneously. In other embodiments, the GW and APR measurements can be performed serially.

Later the MMNTTI system can exploit the synergy between the APR and GW techniques. Some of the defects are identified based on the APR method alone, other types of defects are identified based on the GW method alone, while the rest of the types of defects are identified by both methods. Thus, the analysis of the reflections obtained by both techniques may be cross referenced to obtain results that are more accurate than those which can be obtained from utilizing each technique (GW or APR) in isolation. For example, through holes are detected conclusively by APR, while GW could miss them if they are very small or misjudge them as non-penetrating wall loss defects. Blockages are detected by APR alone. Defects on the outer surface, also known as Outer Diameter (OD), and cracks also, are detected by GW alone. In addition, defects on the internal surface, also known as Internal Diameter (ID), are differentiated from OD defects by the fact that they are detected by both APR and GW. Sizing them can be accomplished with GW signatures, which is more accurate for assessing wall loss defects.

The location of each found defect along the tube can be used in order to correlate results received from the APR system and GW system. However, the reflected signals in both techniques are in the time domain. Therefore, those signals can be transformed into position related signals by an embodiment of MMNTTI. Transforming the time related signals into position related signal is implemented by converting the time axis of the signals to location axis, per each modality. However, the conversion is not simple because the speed of sound depends on the temperature of the air in the tube. Usually the exact temperature in a tube is unknown and can change from one tube to the other. In order to overcome the temperature changes in the APR technique, some embodiments use the measured time of reflection received from the end-of tube (end-of-tube signal) to correlate between the time associated with reflection from a defect and the location of the defect in the current measured tube. The location of each defect is related to the distance between the location of the probe of MMNTTI in the tube and the end-of tube.

The location axis can be normalized to the location of the end-of-tube signal by dividing the receiving time of a reflected signal from a defect by the receiving time of the end-of-tube signal. Thus, "stretching" the signals such that the end-of-tube signal is in the right position (nominal tube length). Throughout the description and the claims, the terms normalized or nominal can be used interchangeably.

In addition, the speed of the mechanical wave in the tube wall depends on the temperature of the tube wall, the structure of the tube (material, the width of the wall, etc.), the frequency and the mode of the mechanical wave. Furthermore, each transducer may generate a plurality of modes and frequencies. Thus, the analysis has to include mode decomposition of the signals. Time-reversal signal processing techniques can be used in order to overcome the dispersion of the mechanical waves, for example.

The resulting position-related signals can be stretched such that the end-of-tube signal is in the right position (nominal tube length). After the "stretching" of the signals, the time axis reflects location of defects in relation to the end-of the tube. The absolute location of each defect is related to the distance between the location of the probe in the tube and the end-of tube. Time-reversal-signal-processing is a well known technique for processing signals received from different type of waves, such as electro/magnetic waves, ultrasonic waves, and acoustic waves, etc.

Next, in an embodiment of an MMNTTI system, defects that are detected using both of the methods (APR and GW) and appear in similar locations in proportion to the location of the end-of the tube (received from APR or GW respectively) can be considered as the same defect. The type of the defect can be determined according to its APR and/or GW signatures.

The end-of-tube signal in each one of the modalities has a unique signature compared to the reflection received from different defects along the tube. In an APR technique, an example signature of a received end-of-tube signal can have the shape of a sharp drop from the baseline, followed by a slower recovery. In GW techniques, an example signature of a received end-of-tube signal can have a shape similar to the excitation signal. Throughout the description and the claims, the terms modality or technique can be used interchangeably.

It should be appreciated that some embodiments are configured to implement the GW technique without the APR modality. In such embodiments, after inserting the probe into an inspected tube, an example embodiment of a GW system may transmit mechanical waves in the tube wall. The mechanical waves can be, but are not limited to, torsional or longitudinal waves. The excitation signal can be, for example but is not limited to, a pulse or a pseudo-noise signal, swept sine, etc. Any changes in the tube wall properties or dimensions will create a reflection which can be recorded and analyzed.

These and other aspects of the disclosure will be apparent in view of the attached figures and detailed description. The foregoing summary is not intended to summarize each potential embodiment or every aspect of the present disclosure, and other features and advantages of the present disclosure will become apparent upon reading the following detailed description of the embodiments with the accompanying drawings and appended claims.

Furthermore, although specific exemplary embodiments are described in detail to illustrate the inventive concepts to a person skilled in the art, such embodiments are susceptible to various modifications and alternative forms. Accordingly, the figures and written description are not intended to limit the scope of the inventive concepts in any manner.

BRIEF DESCRIPTION OF THE DRAWINGS

Some examples of embodiments of the present disclosure will be understood and appreciated more fully from the following detailed description, taken in conjunction with the drawings in which.

DETAILED DESCRIPTION OF DIFFERENT EMBODIMENTS

Turning now to the figures in which like numerals represent like elements throughout the several views, different embodiments of the tube inspection system, as well as features, aspects and functions that may be incorporated into one or more such embodiments, are described. For convenience, only some elements of the same group may be labeled with numerals. The purpose of the drawings is to describe different embodiments and not for production. Therefore features shown in the figures are chosen for convenience and clarity of presentation only. It should be noted that FIGS. 1, 2 and 3a&b are for illustration purposes only and are not drawn to scale. Moreover, the language used in this disclosure has been principally selected for readability and instructional purposes, and may not have been selected to delineate or circumscribe the inventive subject matter, resort to the claims being necessary to determine such inventive subject matter.

Figure 1:
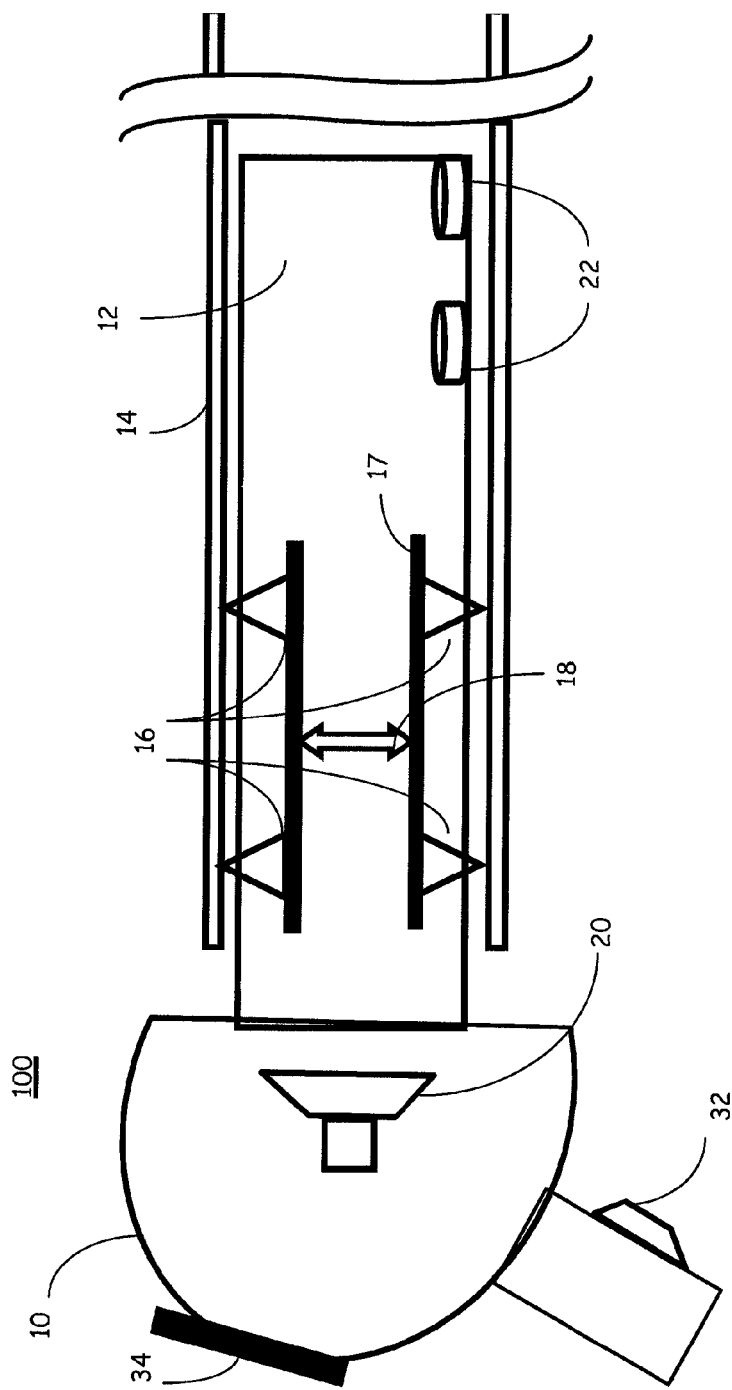
FIG. 1 illustrates relevant elements in a cross-section view of an example of a probe to be inserted into a tube under inspection.

FIG. 1 illustrates an example of a hand-held probe 100 of an MMNTTI. The hand-held probe 100 can comprise a housing 10 to which a transducer cylinder 12 can be either permanently affixed or detachably affixed. The transducer cylinder 12 can be inserted into a near-end of a tube to be inspected 14. The hand-held probe 100 can include or be coupled with a plurality of different sized of transducer cylinders 12, wherein each transducer cylinder could fit a different internal diameter of an inspected tube 14.

An example of a transducer cylinder 12 can comprise a GW transducer mechanism 17, having a plurality of GW transducers 16 and a pressing mechanism 18. The plurality of GW transducers 16 are used for generating the guided waves in the tube under inspection 14 and for receiving the reflected guided waves. The GW transducers 16 can be arranged in two or more rings around the GW transducer mechanism 17. Each ring can comprise a plurality of GW transducers. In some embodiments the rings can have a similar number of transducers. In other possible embodiments each ring can have a different number of transducers. Using the plurality of rings allows for the installation of a large number of GW transducers, several tens for example. However, some embodiments of the tube inspector may comprise as much as 24 to 32, or even more transducers, for example. The large number of GW transducers can be used to control and selectively extract different modes of GW propagation. In some embodiments of the hand-held probe 100, the two or more rings of transducers can be placed with an azimuthal offset relative to each other. Each ring is at a different axial location. The received signals from the different rings can be combined to eliminate unwanted modes. Throughout the description and the claims the two terms circumferential and azimuthal can be used interchangeably.

GW transducers can be, but are not limited to, piezoelectric elements, EMAT (ElectroMagnetic Acoustic Transducer) transducers, magnetostrictive transducers, etc. The pressing mechanism 18 can be used for pressing the transducers 16 against the interior wall of the tube 14 while performing the measurements. In one embodiment, the pressing mechanism 18 can comprise mechanical linkages actuated by an electric motor or air pressure. In another embodiment, the pressing mechanism 18 could be an internal inflatable bladder that would press the GW transducers against the tube wall.

In some embodiments of the GW transducer mechanism 17, the GW transducers can comprise piezoelectric transducers 16. In some cases, at certain frequencies of mechanical vibrations, resonance can occur between the piezoelectric transducers 16 and the tube 14 under test. In order to suppress the resonance between a piezoelectric elements and the wall of the tube under inspection, some embodiments may use a partially-isolating-dry-coupling element. The partially-isolating-dry-coupling element can be added between the transducer and the tube wall for attenuating resonance. Suppressing the resonance conditions facilitates using wide bandwidth (BW) signal. The BW can be in the range of few tens of KHz up to few hundreds, 50 KHz up to 800 KHz width, for example.

As a non-limiting example, the partially-isolating-dry coupling element can be made from a composition of 5-35% of metal powder of diameter in the range of 0.1-50 microns, 10-50% adhesive material, and various additives that modify the mechanical properties. The percentage values are in volume. The metal powder can comprise metal, such as but not limited to, gold, silver, tungsten, or lead. The adhesive material can comprise epoxies resin, RTV, contact glue, etc. The additives can comprise material such as but not limited to polymers (e.g. PVC, polystyrene, polyamide), elastomers (latex, Nitrile rubber EPDM etc), organic solvents and diluents.

The partially-isolating-dry coupling element may suppress the mechanical resonances between the transducer 16 and the tube 14 and prevent resonance at the required high frequency while increasing the useful bandwidth. In order to raise the signal to noise ratio, embodiments of the hand-held probe 100 can overcome the attenuation of the absorbing element on the signal to noise ratio of the GW signals by increasing the mechanical energy delivered from the transducers 16. Along the description the terms "absorbing element"; "partially-isolating-dry coupling element" can be used interchangeably.

The hand-held probe (HHP) 100 can comprise a speaker 20, such as a loudspeaker as a non-limiting example that creates the acoustic wave for the APR system. Loudspeaker 20 could be either in the housing 10 or in the transducer cylinder 12. A microphone or a plurality of microphones 22 can be associated with the housing 10 or the transducer cylinder 12. The one or more microphones 22 can receive the acoustic waves traveling along the transducer cylinder 12 and convert them into electronic signals. The acoustic waves can be the acoustic waves created by the loudspeaker 20 as well as reflections created in the inspected tube 14.

In some embodiments, the housing 10 can comprise one or more control buttons 32 or a keyboard for initiating measurements and entering data. It may also have a display unit 34 for conveying information to the user.

Yet in other embodiments, not shown in the drawings, a hand-held probe can be adapted to employ the GW technique alone. Such a hand-held probe may not comprise the loudspeaker and the microphone or a plurality of microphones.

In more detail, the housing 10 is used to insert the transducer cylinder 12 into the interior of a tube under inspection 14. The pressing mechanism 18 is then initiated to hold the GW transducers 16 into place against the internal surface of inspected tube 14. A sequence of measurements is then initiated, using both the APR and the GW elements, either in conjunction (simultaneously) or sequentially. Applying the GW technique, one or more of transducers 16 serve as actuators that function to create the wave, while one or more of the remaining transducers 16 serve as receivers. In one embodiment, several GW measurements can be carried out, where the transducers 16 serve alternatively as either actuators or receivers, or perform both tasks at the same time. All received mechanical signals are converted into electronic signals by the one or more transducers 16. The electronic signals can be transmitted or communicated to an MPU 226, via cable 224, (FIG. 2) where they can be stored, or analyzed in real time, or both.

While activating the APR technique, the loudspeaker 20 excites an acoustic signal, either directly within the tube under inspection 14 if the loudspeaker 20 is located in side the transducer cylinder 12, or injects the acoustic signal into the tube under inspection 14 from the hand held unit 10 if the loudspeaker 20 is located within the hand held unit 10. Microphone or microphones 22 receive this signal and the ensuing reflections created in the tube under inspection 14. All received acoustic signals are converted into electronic signals by the one or more microphones 22. The electronic signals can be transmitted to the MPU 226, via cable 224, (FIG. 2) where they can be stored, or analyzed in real time, or both.

In some embodiments, the transducer cylinder 12 is configured to enable the propagation of the acoustic wave from the loudspeaker 20, which is located in the housing 10, via the transducer cylinder 12 toward the interior of the tube under inspection. Thus, if the loudspeaker 20 is towards the back of the transducer cylinder 12 or in the hand held unit 100 itself, thus, the GW transducer mechanism 17 with its various transducers 16 and pressing mechanism 18 do not obstruct this acoustic path. In other embodiments, not shown in the drawings, the loudspeaker can be located at the front of the transducer cylinder 12. In some embodiments the length of transducer cylinder 12 is such that it penetrates the end of the tube under inspection 14 that is held by a tube sheet, and places the transducers 16 far enough into the tube to be in contact with a portion of the tube not inside the tube sheet.

In some embodiments, a detachable transducer cylinder 12 can have a shape of a cylinder with a near end and a far end. The detachable transducer cylinder 12 can comprise a GW transducer mechanism 17 having a plurality of GW transducers 16 and a pressing mechanism 18 for pressing them against the interior wall of the tube, and one or more microphones 22. The diameter of the cylinder is less than the internal diameter (ID) of the tube under inspection 14. The near end of the detachable transducer cylinder 12 can comprise an adaptor (not shown in the drawings) that fits in one side the diameter of the opening of the housing 10 and on the other-side is adapted to the diameter of the detachable transducer cylinder 12. This adaptor can be referred to as a cylinder-housing-diameter-adaptation mechanism. Further, the adaptor includes a locking mechanism to lock the cylinder into place. The locking mechanism can include a threaded lock, a snapping lock or any of a variety of other mechanisms. A plurality of detachable transducer cylinders can be associated with the HHP 100. Each detachable transducer cylinder 12 can relate to a certain range of diameters of an inspected tube. An exemplary adaptor can comprise a threaded retainer and an electronic connector for attaching and detaching from the housing 10, for example.

Yet in other embodiments, not shown in the drawings, the detachable transducer cylinders 12 can comprise a loudspeaker. In such embodiments, the pressing mechanism 18 can be located first, when looking from the housing side. Following the pressing mechanism 18 a loudspeaker can be installed and finally the one or more microphones can be located after the loudspeaker. An example of such embodiment can include isolation between the guided-wave (GW) transducer pressing mechanism 18 and the APR transducers (the loudspeaker and the one or more microphones). The APR transducer can be mechanically and acoustically isolated from the wall of the transducer cylinder 12.

In the illustrated embodiment in FIG. 1, the loudspeaker 20 (which can be any form of audio source), the opening in the housing 10 that receives the transducer cylinder 12, the transducers 16 and the pressing mechanism 18 are all illustrated as being substantially coaxially aligned in that the radial center of each of these elements are substantially aligned along the same axis. However, in other embodiments, one or more of these elements may be skewed or located in a manner that is not so aligned.

Figure 2:
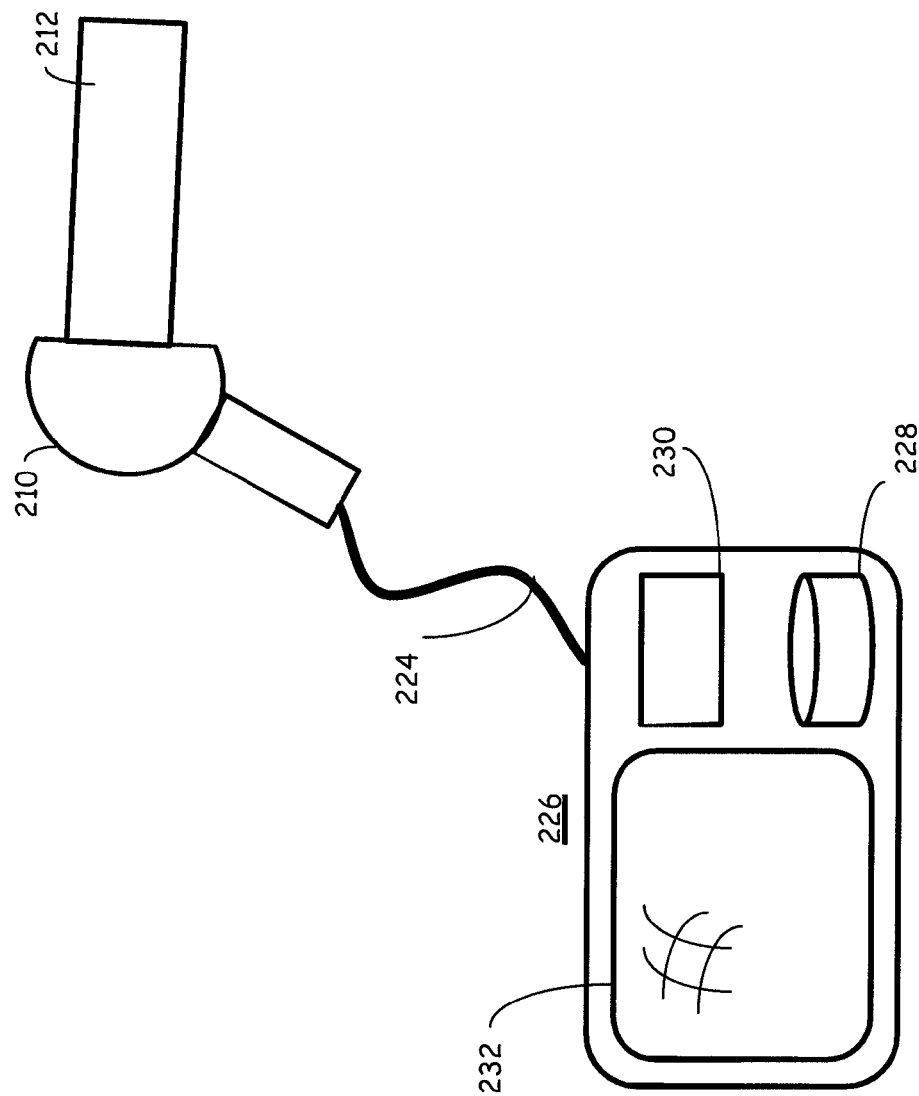
FIG. 2 shows relevant elements of an example of an MMNTTI system.

FIG. 2 illustrates another example of an MMNTTI having a HHP with a housing 210 and transducer cylinder 212 connected by a cable 224 to a main processing unit (MPU) 226. The cable 224 carries the signals between the housing 210 and the MPU 226. The MPU 226 can generate and transmit, via the cable 224, the electrical excitation signals toward the GW elements (transducer 16 in FIG. 1) and the APR elements (loudspeaker 20) at the HHP 100 (FIG. 1). The electronic signals from the microphones 22 and transducers 16 can be carried over cable 224 to the MPU 226. In some embodiments, the cable 224 can comprise pressure and/or vacuum lines for pressing mechanism 18 to be actuated and thus press the transducers 16 against the wall of the tube under inspection 14 (FIG. 1). The MPU 226 may comprise a storage medium 228 for recording the signals, software, reports, etc. addition, MPU 226 may comprise a processor 230. The processor 230 can be loaded from the storage medium 228 with software in order to execute the necessary processes for measuring the condition of the inspected tube, collecting the received signals, processing them, analyzing them, and delivering reports or output information to a display 232. The display unit 232 can be used as an interface between a user and the MPU 226. In addition MPU 226 can be connected to a printer in order to deliver printed reports.

Figures 3A, 3B:
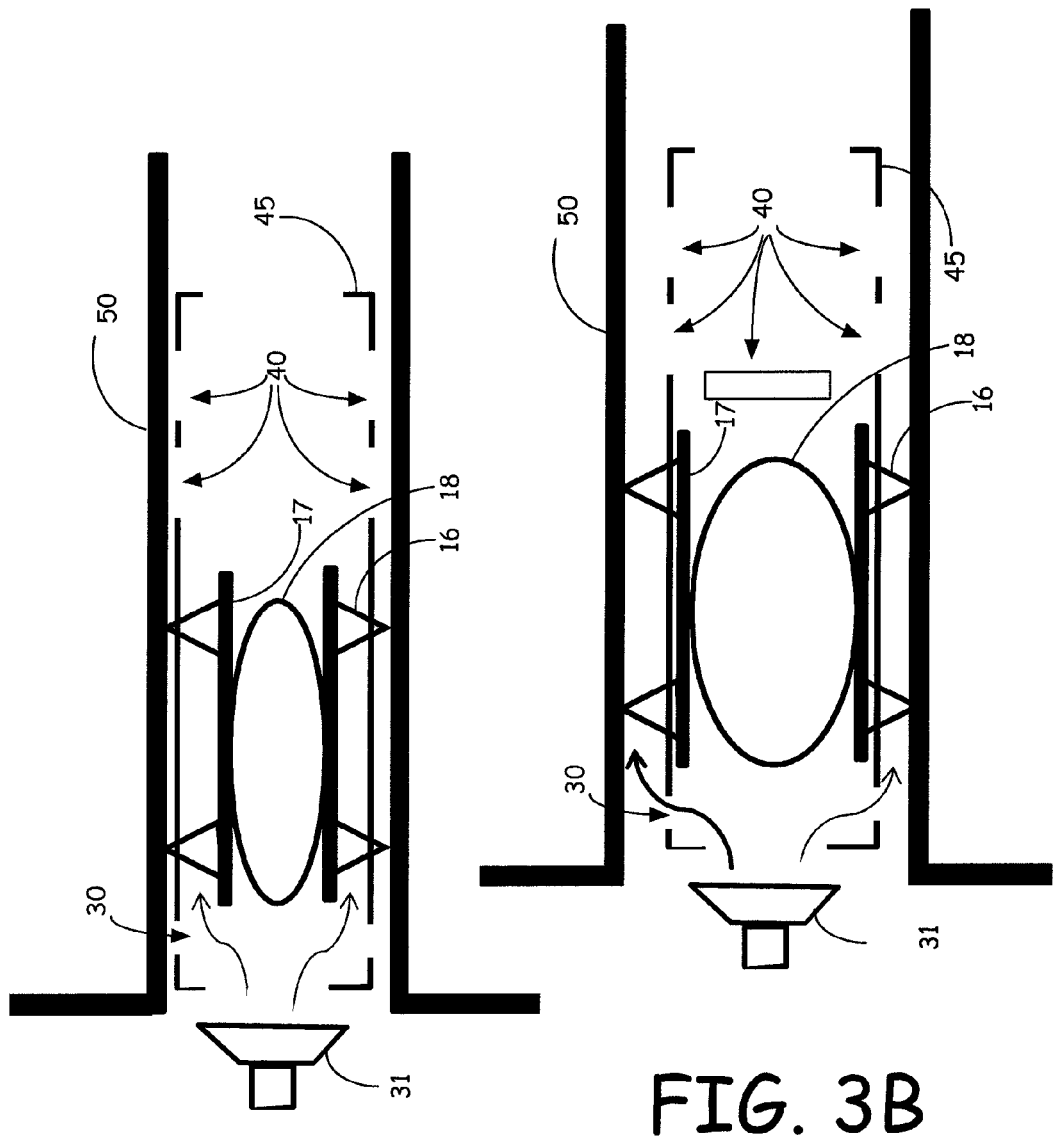
FIG. 3a shows an example of an acoustic pathway when measuring a tube that is narrow in comparison to the transducer cylinder.
FIG. 3b shows an example of an acoustic pathway when measuring a tube that is wide in comparison to the transducer cylinder.

FIG. 3A and FIG. 3B illustrate an example structure of a transducer cylinder 45 of an MMNTTI in a near end of a tube 50. The transducer cylinder 45 can comprise a GW transducer mechanism 17 with its pressing mechanism 18 and the GW transducers 16. The GW transducer mechanism 17 is located between the loudspeaker 31 and the one or more microphones (not shown in FIG. 3A and FIG. 3B) of the APR technique. The example of the transducer cylinder 45 can have two sets of slots 30 and 40 along the circumference of cylinder 45. The first set of slots 30 can be located before the GW transducer mechanism 17. The second set of slots 40 can be located after the GW transducer mechanism 17. The two sets of slots, 30 and 40, provide an acoustic path between the loudspeaker 31 and the one or more microphones of the APR technique and the inside of tube 50.

As it is illustrated in FIG. 3A and FIG. 3B, the acoustic path is self adapted to the diameter of the inspected tube 50. FIG. 3A illustrates a case in which the inspected tube 50 is narrow, slightly wider than transducer cylinder 45, in such a case the acoustic path, between the loudspeaker 31 and the one or more microphones and the inside of tube 50, is established between the GW transducer pressing mechanism 18 and the wall of the transducer cylinder. FIG. 3B describes the case where the tube under inspection 50 is significantly wider than transducer cylinder 45, thus the transducers 16 protrude far outside of the outer diameter of the transducer cylinder 45. In this case the acoustic pathway is provided from the loudspeaker, through openings 30 in the transducer cylinder 45 and between the walls of the tube under inspection 50 and the transducer cylinder 45 and back via openings 40 toward the inside of tube 50. In some embodiments the openings 30 and 40 have the shape of slots, in other embodiment openings 30 and 40 can have the shapes of holes or any other shape, for example. For cases that the diameter of the inspected tube is in between the two sizes, then the acoustic path can be divided into two paths, one in between the walls of the inspected tube and the transducer cylinder and the second path in between the wall of the transducer cylinder and the GW transducer mechanism 17. In another example of MMNTTI (not shown in the drawings) only one set of one or more slots is used, slots 30, for example.

Yet in other embodiments, not shown in the drawings, in which a hand-held probe is adapted to employ the GW technique alone. Such a hand-held probe may not have the slots 30 and 40 because there is no need for an acoustic pathway.

In an example of an MMNTTI system, as illustrated in FIG. 1, in which the GW transducer mechanism 17 is located between a loudspeaker 20 and one or more microphones 22 of the APR section, then multiple reflections from the components of the GW transducer mechanism 17 will be created and recorded by the one or more microphones 22. The multiple reflections can obscure reflections from actual defects in the tube under inspection 14 and reduce the sensitivity of the system. In some embodiments of MMNTTI systems in which a single microphone is used, a calibration is needed in order to reduce the effect created by the GW transducer mechanism 17 on the reading of the APR section. However, the calibration is sensitive to temperature variations enforcing frequent calibrations. In other embodiments of MMNTTI systems, multiple microphones 22 are used. Processing the reflections received from the two or more microphones 22 enables separation of right and left propagating waves, thus enabling the elimination of some of the spurious reflections.

In some embodiments of MMNTTI the GW and APR measurements can be performed simultaneously. In other embodiments, the GW and APR measurements can be performed serially. Once the APR and GW measurements have been performed, their complementary properties can be exploited to give results that are better than when each method is implemented alone. APR is highly accurate at detecting and sizing of blockages in the tube being inspected 14, as well as pinholes down to approximately 0.5 mm in diameter. On the other hand, because APR is sensitive to changes in the cross section of the tube, it is less accurate at detecting and sizing small wall loss defects, which present very small changes in overall internal cross section. APR is also limited to detection of wall loss on the ID only. The GW technique is not sensitive to blockages, but can detect wall loss defects on both the ID and OD, in addition to detecting cracks. Cross referencing the GW measurements with the APR measurements can be useful in determining whether defects are on the ID or OD, since defects found by both methods can only be on the ID. GW is more sensitive to small ID defects than APR and can size them more accurately.

Figure 4:
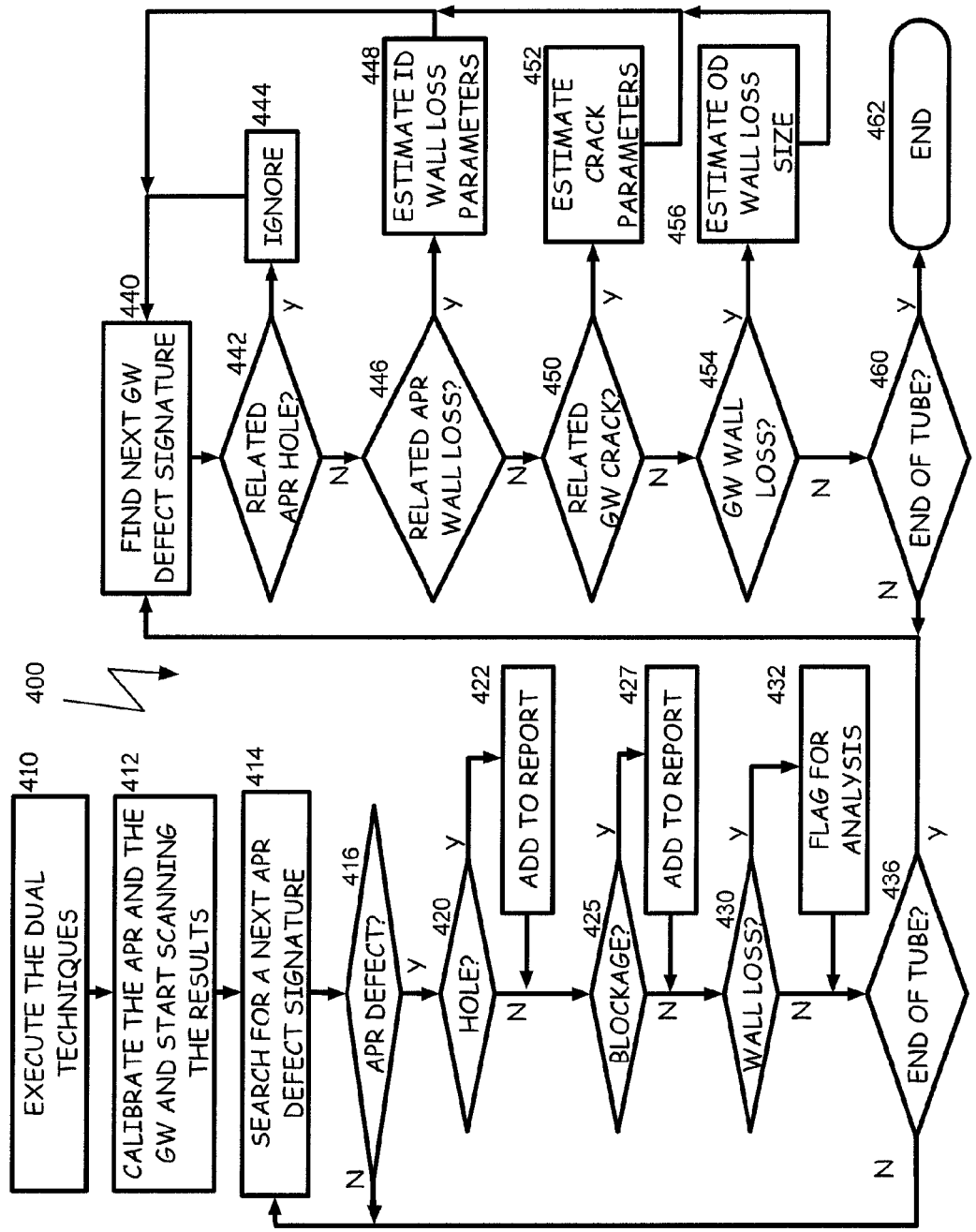
FIG. 4 shows a flowchart with relevant actions of an example process of analyzing the results to determine flaw types and sizes.

FIG. 4 illustrates a flowchart with relevant actions of an embodiment of process 400. Process 400 can be used for scanning through the stored measurements obtained by a hand-held probe, analyzing the results including exploiting the synergy between the APR and GW for detecting defects and defining the type and the size of each defect. Process 400 can be implemented by processor 230 (FIG. 2) after loading stored programs from the storage medium 228. The process 400 can be initiated 410 each time the hand-held probe 100 is inserted into a tube and the user actuates the button 32 (FIG. 1) to initiate the inspection process. Upon initiation 410, an example of the process 400 may be configured to allocate storage resources in the storage medium 228 for storing the results of the measurement and a report data based on the results of the measurements. Next, the process 400 may implement the APR modality first and transmit an acoustic wave via the loudspeaker 31, slots 30, 40 and/or between the transducers 16. The reflected acoustic waves are received by one or more microphones 22, converted to electrical signals that are transferred to and are stored by the MPU 226 (FIG. 2). Aspects of the APR method are well known to a person having ordinary skill in the art and, the reader who wishes to learn more about APR is invited to read U.S. Pat. No. 7,677,103, or US patent application publication US 2011/0,112,776; US20110320139(A1); US20120053895(A1) or US2011-0166808.

Next, the GW modality can be implemented. Wide band mechanical waves can be transmitted from one or more of the plurality of transducers 16 on each of the rings. The transmitted signal can be in the range of a few tens to few hundreds of KHz (50-800 KHz, for example). In some embodiments, the transmitted signal can be pseudorandom noise. The axial shift between the transducer rings may be 30 mm. The reflected mechanical waves can be received by the one or more transducers 16 and be converted into electrical signals that are transferred toward and are stored by the MPU 226 (FIG. 2). Aspects of the GW method re well known to a person having ordinary skill in the art and, the reader who wishes to learn more about GW is invited to read U.S. Pat. Nos. 7,019,520; 7,634,392, or US patent application publication US2009/0,158,850 or PCT publication WO1996/012,951 and many others.

In some embodiments, each of the transducers 16 can represent a set of two or more GW transducers. Comparing between the signals received from the two or more transducers in a set can be used in order to control and selectively extract the right and left propagating waves. Another embodiment of the MMNTTI may initially start with only the GW technique and then subsequently add in the ARP. Yet, another alternate embodiment may implement the two techniques simultaneously. Further, some embodiments may implement the GW and the ARP techniques simultaneously for a period of time and then implement one and then the other during other periods of time.

In some embodiments the measurement preformed in block 410 can be executed several times in order to filter noise, for example. An average or median, for example, can be used in order to remove random noise effects.

Next, at block 412 the end-of-tube signal can be searched for each modality in order to calibrate the two modalities, the APR and the GW, to the length of the tube. The time of receiving the end-of-tube signal for each technique can be used as a reference to normalize the time measurement of reflected signals of both techniques to the length of the tube. Thus, the time domain APR signals and GW signals that represent the reflected waves from the different defects along the tube can be normalized to the length of the tube. The time scale of each measurement is thus stretched to a normalized time or nominal time of receiving of the end-of-tube signal in the relevant measurement cycle.

In a system that comprises a hand held probe that is configured to employ the GW technique alone, the actions that are described above in conjunction to blocks 410 and 412 can be limited only to the GW technique.

At the end of calibrating both modalities, the received signal that was generated by the APR section of an example embodiment of an MMNTTI, after being processed and normalized according to the receiving time of the end-of-tube signal, can be analyzed looking for a shape of a signal that represent the signature of a defect. The analyses can be done in two loops. A first loop can be implemented on the APR results as depicted in actions 414 to 436. The second loop can be implemented on the GW results as depicted in actions 440 to 460.

Thus, the process continues by searching for either APR defect signatures or GW defect signatures. Although either search can be conducted first or both searches can be conducted simultaneously, the present embodiment will be described as processing the APR defects first. As such, action 414 includes searching for a next APR defect signature.

Upon detecting 416 a signature of an APR defect, a decision is made whether 420 the signature is a signature of a hole. If the signature is that of a hole, then the nominal time of the signature can be stored 422 as an index in the report and the type of the defect as a hole and information about the hole can be stored in the report. The process 400 then proceeds to block 425 to make further analysis of the defect signal.

After examining the defect to determine if it is a hole 420, then the signature is further analyzed to determine whether 425 the signature is a signature of a blockage. If the signature is that of a blockage, then the nominal time of the signature can be stored 427 as an index in the report and the type of the defect as a blockage and information about the blockage can be stored in the report and method 400. The process then proceeds to block 430 to make further analysis of the defect signal in some embodiments or, proceeds to action 436 in other embodiments (not shown in the drawings).

At block 430 a decision is made whether the signature is a signature of a "wall loss". If 430 the signature indicates there is a wall loss, then the nominal time of the signature can be stored 432 as an index in the report and the type of the defect as a "wall loss" with information about the "wall loss" can be stored in the report and in addition, a flag for further analysis can be set to true. The process 400 then proceeds to block 436.

After analyzing the type of defect signature, then a decision is made whether 436 the signature represents that the end-of-tube has been reached. If 436 the signature does not indicated that the end of the tube has been reached, the process 400 returns to block 414 looking for the next signature. However, if 436 the signature indicates that the end of the tube has been reached, then in the illustrated embodiment, the second loop can be initiated 440 and process 400 may start searching 440 the processed results received from the GW technique looking for the next signature of a defect in the GW stored results starting from the beginning of the tube.

Upon finding a GW signature of a defect 440, the report of the defects that was created in the first loop, the APR loop, is checked looking for a reported APR defect that is related to similar normalized time. If a related APR defect has been previously reported, the process determines whether 442 the related APR defect was reported as a hole. If 442 the related APR defect is actually reported as a hole, then the GW signature can be ignored 444 and the process 400 returns to block 440 looking for the next GW signature of a defect.

However, if at decision block 442 it is determined that the related defect in the report of the defects that was created in the first loop, the APR loop, was not reported as a hole, then the process 400 continues by determining 446 whether the related defect in the APR report (having similar nominal time) was flagged as "wall loss". If 446 the related APR defect was not flagged as "wall loss", the process 400 proceeds to decision block 450. However, if 446 the related APR defect was flagged as a "wall loss", which means that the wall loss is Internal Diameter (ID) wall loss. In addition at block 448, based on the signature of the related defect in the GW signal, parameters of the "ID wall lose" can be estimated. As a non-limiting example of such a parameter, the area and depth of the "ID wall loss" can be estimated. The estimated parameters can be stored in the reported table in the same entry as the related APR defect according to the nominal time and the process 400 can return to block 440.

At block 450, the process 400 continues by determining whether the related GW signature reflects a signature of a crack. If 450 the related GW signature was not reported as a crack, the process 400 may proceed to block 454. However, if 450 the related signature reflects a signature of a crack, then at block 452, based on the GW signature, parameters of the crack can be estimated. As a non-limiting example of such a parameter, the depth, width and/or length of the crack can be estimated. A new entry in the defect report can be allocated having an index that is related to the nominal time of the GW signature of the crack and the estimated parameters of the crack and, the new entry can be stored in the reported table in that entry. Then, the process 400 returns to block 440.

At block 454, the process determines whether the related signature reflects a GW signature of a "wall loss". If 454 it is not a "wall loss", then the process 400 may proceed to block 460. If 454 the related GW signature reflects a signature of a "wall loss", which means that the wall loss is an Outer Diameter (OD) wall loss. In addition at block 456 based on the GW signature, parameters of the "OD wall loss" can be estimated. Parameters such as the size of the "OD wall loss" for example. A new entry in the defect report can be allocated having an index that is related to the nominal time of the GW signature of the "OD wall loss" and the estimated parameters of the "OD wall loss" can be stored in the reported table in that entry. Then, the process 400 proceeds to block 460.

At block 460, the process 400 operates to determine if the most recently detected GW signature reflects the GW signature of the end-of-tube signal. If the signal indicates that it is a reflection from the end of the tube being inspected, the process 400 can be terminated and the report of the defects can be further analyzed for defining the status of the tube under inspection. If 460 the GW signature is not the reflected GW signature of the end-of-tube, then the process 400 returns to block 440 looking for a next GW signature.

It should be appreciated that the process 400 can be adapted to operate with a hand held probe that only includes GW transducers without any APR transducers. In such embodiments, the actions related to the loop between blocks 414 and 436 can be eliminated. Further, the actions that are related to the second loop between blocks 440 and 460 can be executed based on the GW results only.

When the results of both methods are treated together, an overall picture is obtained that is more comprehensive than what would be obtained from using each technique separately. The two methods, GW and APR, when combined, can detect the full range of typical flaws in tubes: blockages, wall loss on the ID and OD, cracks and through holes. Furthermore, cross referencing the results can resolve ambiguities. For instance, a very small hole might show up as a very small wall loss indication in a GW measurement, but would give a large indication typical to a hole in the APR measurement. On the other hand, a small wall loss defect would give a very small reading in an APR measurement, which might be confused with background noise, but would give a much larger reading in the GW measurement. Wall loss indications found only by GW could be deduced to be on the OD, while wall loss indications given by both methods could be deduced to be on the ID, etc.

Embodiments of the present disclosure teach how to combine APR elements and GW elements into a single tube inspection multi-modality system. The novel tube inspection system performs both types of measurements on each tube to be inspected. Indications from both types of measurements are combined in a manner that allows them to complement each other. On the one hand, each method can detect some defects which the other cannot, and where their capabilities overlap the results of one method can be used to reinforce the results of the other.

Further, some embodiments of the present disclosure teach how to build and improve a hand-held probe that is adapted to execute the GW modality with higher resolution.

The above description is intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled. In the appended claims, the terms "including" and "in which" are used as the plain-English equivalents of the respective terms "comprising" and "wherein".

What is claimed is:

1. A method for inspecting the condition of a tube utilizing a probe device that comprises a transducer element, the method comprising:
   communicating an acoustic wave toward a tube such that at least a portion of the communicated acoustic wave propagates within the interior of the tube;
   receiving reflections of the acoustic wave and converting them into electronic signals;
   communicating a mechanical wave such that at least a portion of the mechanical waves propagate inside the wall of the tube;
   receiving reflections of the mechanical wave and converting them into electronic signals;
   communicating the converted electronic signals of the acoustic wave and mechanical wave reflections to a processing device; and
   processing the received electronic signals to detect locations, types and size of flaws in the tube;
   wherein said processing comprises:
      comparing the locations and types of flaws detected from said processing of the reflected acoustic waves electronic signals with locations and types of flaws detected from processing of the reflected mechanical waves electronic signals; and
      concluding that a flaw is a non-penetrating crack or Outer Diameter (OD) wall loss if the flaw appears only in the electronic signals created from the mechanical wave reflections in the wall of the tube.

2. The method of claim 1, comprising at least partially inserting the probe device into the interior of the tube.

3. The method of claim 1, wherein comparing the results further comprising normalizing the timing of each received signal to the time of receiving a signal from a far end of the tube.

4. The method of claim 1, wherein communicating acoustic waves and communicating mechanical waves are implemented in serial.

5. The method of claim 1, wherein the acoustic wave comprises an acoustic pseudo noise signal.

6. A hand-held probe (HHP) for inspecting a tube, the HHP comprising:
   a transducer cylinder having a shape of a cylinder with a near end and a far end and comprising a mechanical wave transducer mechanism with a plurality of mechanical wave transducers organized in two or more rings;
   a housing having an opening configured for receiving the near end of the transducer cylinder;
   a processing unit configured and operable for receiving the converted electronic signals of the acoustic wave and mechanical wave reflections from said transducer cylinder and processing the received electronic signals to detect locations, types and size of flaws in the tube;
   wherein said processing unit is configured and operable for comparing the locations and types of flaws detected from processing the reflected acoustic waves electronic signals with locations and types of flaws detected from processing the reflected mechanical waves electronic signals; and concluding that a flaw is a non-penetrating crack or Outer Diameter (OD) wall loss if the flaw appears only in the electronic signals created from the mechanical wave reflections in the wall of the tube;
   wherein, when the transducer cylinder is inserted into the tube, the transducer mechanism presses the plurality of the mechanical-wave transducers toward the interior wall of the tube such that the transducer cylinder is configured to communicate a mechanical wave toward the wall of the tube and receive reflections of the mechanical wave caused by anomalies in the wall of the tube.

7. The HHP of claim 6, wherein said transducer cylinder is configured and operable for receiving reflections of the acoustic wave and converting them into electronic signals and receiving reflections of the mechanical wave and converting them into electronic signals.

8. The HHP of claim 6, wherein said processing unit is configured and operable for comparing the results further comprising normalizing the timing of each received signal to the time of receiving a signal from a far end of the tube.

9. The HHP of claim 6, wherein said mechanical wave transducer mechanism comprises a pressing mechanism configured for pressing the plurality of the mechanical-wave transducers toward the interior wall of the tube prior to the transducer cylinder communicating a mechanical wave toward the interior wall of the tube and receiving reflections of mechanical waves from the interior wall of the tube.

10. The HHP of claim 6, comprising a loudspeaker configured and operable for creating and transmitting an acoustic wave toward the inside of the tube.

11. The HHP of claim 6, wherein said transducer cylinder comprises one or more microphones configured for receiving reflections of the acoustic wave from anomalies in the interior of the tube.

12. The HHP of claim 6, wherein each ring has different number of mechanical wave transducers, or each ring comprise a plurality of mechanical wave transducers, or each ring is at a different axial location relative to each other.

13. The HHP of claim 6, wherein the two or more rings are placed with a circumferential offset relative to each other.

* * * * *